United States Patent
Preston et al.

(10) Patent No.: US 12,111,281 B2
(45) Date of Patent: Oct. 8, 2024

(54) HYDROGEN CONCENTRATION SENSOR

(71) Applicant: DOOSAN FUEL CELL AMERICA, INC., South Windsor, CT (US)

(72) Inventors: Joshua Preston, South Windsor, CT (US); Timothy William Patterson, Jr., West Hartford, CT (US)

(73) Assignee: HYAXIOM, INC., East Hartford, CT (US)

( * ) Notice: Subject to any disclaimer, the term of this patent is extended or adjusted under 35 U.S.C. 154(b) by 704 days.

(21) Appl. No.: 16/198,044

(22) Filed: Nov. 21, 2018

(65) Prior Publication Data

US 2020/0158683 A1    May 21, 2020

(51) Int. Cl.
*G01N 27/407* (2006.01)
(52) U.S. Cl.
CPC ....... *G01N 27/407* (2013.01); *G01N 27/4074* (2013.01)
(58) Field of Classification Search
CPC ............ G01N 27/407; G01N 27/4074; G01N 27/417; G01N 33/0059; G01N 33/005; G01N 27/406–41; G01N 33/0004–0075
See application file for complete search history.

(56) References Cited

U.S. PATENT DOCUMENTS

| | | | |
|---|---|---|---|
| 4,025,412 A * | 5/1977 | LaConti | G01N 27/4045 204/424 |
| 4,051,006 A | 9/1977 | Neti et al. | |
| 4,731,211 A | 3/1988 | Lee | |
| 4,766,044 A | 8/1988 | Sederquist | |
| 4,859,305 A | 8/1989 | Schneider et al. | |
| 4,859,307 A | 8/1989 | Nishizawa et al. | |
| 4,895,775 A | 1/1990 | Kato et al. | |
| 5,547,554 A | 8/1996 | Kiesele | |
| 5,667,653 A | 9/1997 | Schneider et al. | |

(Continued)

FOREIGN PATENT DOCUMENTS

| CN | 207558943 U | 6/2018 |
|---|---|---|
| JP | H05275097 A | 10/1993 |

(Continued)

OTHER PUBLICATIONS

Koji et al. (JP 2000/131273 A, machine translation) (Year: 2000).*

(Continued)

*Primary Examiner* — Luan V Van
*Assistant Examiner* — Shizhi Qian
(74) *Attorney, Agent, or Firm* — Carlson, Gaskey & Olds, P.C.

(57) ABSTRACT

An illustrative example hydrogen concentration sensor includes a hydrogen chamber configured to isolate hydrogen within the hydrogen chamber from gas outside the hydrogen chamber. A hydrogen evolving electrode is configured to generate pure hydrogen within the hydrogen chamber. A reference electrode is situated to be exposed to pure hydrogen within the hydrogen chamber. A detection electrode associated with the reference electrode is situated to be exposed to gas outside the hydrogen chamber. The detection electrode is configured to provide an indication of a concentration of hydrogen in the gas outside the hydrogen chamber.

13 Claims, 1 Drawing Sheet

(56) References Cited

U.S. PATENT DOCUMENTS

| | | | |
|---|---|---|---|
| 5,668,302 A | 9/1997 | Finbow et al. | |
| 6,168,705 B1 | 1/2001 | Molter et al. | |
| 6,280,865 B1 | 8/2001 | Eisman et al. | |
| 6,368,735 B1 | 4/2002 | Lomax et al. | |
| 6,376,124 B1 | 4/2002 | Dodgson et al. | |
| 6,455,181 B1 | 9/2002 | Hallum | |
| 6,495,277 B1* | 12/2002 | Edlund | H01M 8/04626 429/411 |
| 6,506,296 B2 | 1/2003 | Babes-Domea et al. | |
| 6,558,519 B1 | 5/2003 | Dodgson et al. | |
| 6,638,416 B2 | 10/2003 | Wang et al. | |
| 6,645,361 B1 | 11/2003 | Bloemer et al. | |
| 6,977,121 B2 | 12/2005 | Balliet et al. | |
| 6,984,464 B2 | 1/2006 | Margiott et al. | |
| 8,298,712 B2 | 10/2012 | Shirakawa | |
| 8,747,635 B2 | 6/2014 | Murakami et al. | |
| 8,771,490 B2 | 7/2014 | Bordo et al. | |
| 8,840,775 B2 | 9/2014 | Chen et al. | |
| 8,932,772 B2 | 1/2015 | Kumei et al. | |
| 9,410,919 B2 | 8/2016 | Spong et al. | |
| 10,062,915 B2 | 8/2018 | Paganelli | |
| 2001/0051290 A1 | 12/2001 | Kashiwagi | |
| 2002/0092780 A1 | 7/2002 | Nadanami et al. | |
| 2003/0158273 A1 | 8/2003 | Kosako et al. | |
| 2004/0028967 A1 | 2/2004 | Katsuki et al. | |
| 2004/0182705 A1 | 9/2004 | Ishikawa et al. | |
| 2004/0197621 A1* | 10/2004 | Balliet | H01M 8/04462 429/427 |
| 2004/0261500 A1* | 12/2004 | Ng | B82Y 15/00 73/31.05 |
| 2005/0042485 A1 | 2/2005 | Murayama | |
| 2005/0153180 A1 | 7/2005 | Hsu | |
| 2005/0181262 A1 | 8/2005 | Vanderleeden et al. | |
| 2005/0214603 A1 | 9/2005 | Barton et al. | |
| 2006/0032742 A1 | 2/2006 | Babes-Domea et al. | |
| 2006/0073373 A1 | 4/2006 | Andrin et al. | |
| 2007/0190380 A1* | 8/2007 | DeVries | H01M 8/04373 429/411 |
| 2008/0145722 A1 | 6/2008 | Coignet et al. | |
| 2008/0179199 A1 | 7/2008 | Coignet et al. | |
| 2008/0223516 A1 | 9/2008 | Tanuma | |
| 2009/0004551 A1 | 1/2009 | Burdzy et al. | |
| 2009/0092883 A1* | 4/2009 | Ozeki | H01M 8/04052 429/425 |
| 2009/0136793 A1 | 5/2009 | Kanno | |
| 2009/0166197 A1 | 7/2009 | Grincourt et al. | |
| 2010/0028730 A1 | 2/2010 | Ghezel-Ayagh et al. | |
| 2011/0151345 A1 | 6/2011 | Lundblad et al. | |
| 2011/0212375 A1* | 9/2011 | Taguchi | H01M 8/0618 429/425 |
| 2014/0251834 A1 | 9/2014 | Chen et al. | |
| 2014/0311905 A1 | 10/2014 | Stetter et al. | |
| 2017/0025692 A1 | 1/2017 | Zhang et al. | |

FOREIGN PATENT DOCUMENTS

| | | | |
|---|---|---|---|
| JP | 2000131273 | | 5/2000 |
| JP | 2000131273 A | * | 5/2000 |
| JP | 2003192309 A | * | 7/2003 |
| JP | 2005332610 | | 12/2005 |
| JP | 2005332610 A | | 12/2005 |
| JP | 2009217951 A | | 9/2009 |
| JP | 2014199233 A | | 10/2014 |
| JP | 2015144092 | | 8/2015 |
| JP | 2015144092 A | | 8/2015 |
| WO | 9409520 | | 4/1994 |
| WO | WO2008048270 A1 | | 4/2008 |
| WO | 2011008898 A2 | | 1/2011 |
| WO | 2018/209082 A1 | | 5/2017 |
| WO | 2019/073850 A1 | | 4/2019 |

OTHER PUBLICATIONS

Onuma et al. (JP 2003192309 A, machine translation) (Year: 2003).*
The International Search Report and Written Opinion for PCT Application No. PCT/US2019/059768, dated Jan. 21, 2020.
International Search Report and Written Opinion of the International Searching Authority for PCT Application No. PCT/2020/027136 dated Jul. 28, 2020.
Cosa+Xentaur, Continuous Hydrogen Analyzer, 2004 COSA Instrument Corporation.
International Search Report and Written Opinion of the International Searching Authority for International application No. PCT/US2021/058217 dated Feb. 8, 2022.
International Search Report and Written Opinion of the International Searching Authority for International application No. PCT/US2021/058186 dated Feb. 8, 2022.
Notice of Preliminary Rejection, Korean Patent Application No. 10-2021-7018973 dated May 31, 2023.
International Preliminary Report on Patentability for International application No. PCT/US2021/058217 dated Jun. 22, 2023.
International Preliminary Report on Patentability for International application No. PCT/US2021/058186 dated Jun. 22, 2023.

* cited by examiner

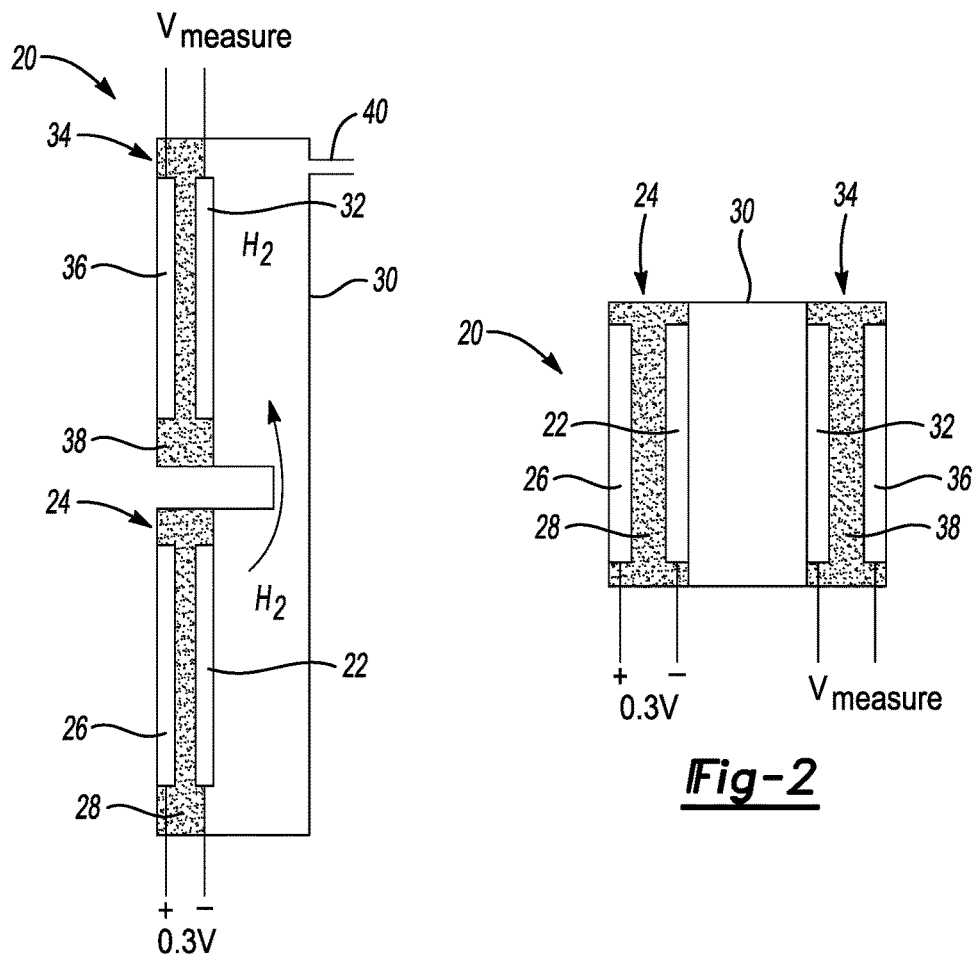
Fig-1
Fig-2
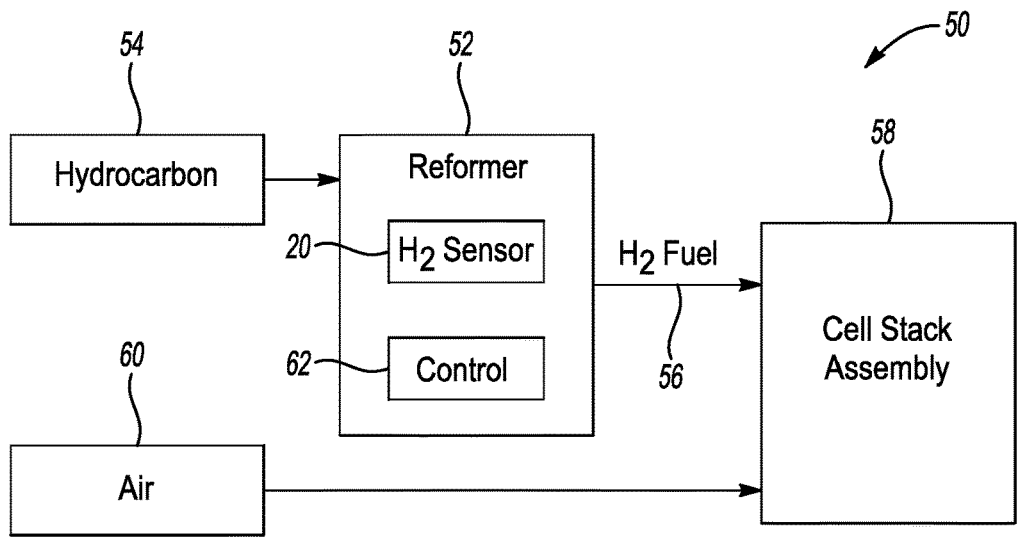
Fig-3

HYDROGEN CONCENTRATION SENSOR

BACKGROUND

Various devices and processes depend on hydrogen for proper operation. For example, fuel cells typically use hydrogen as a reactant fuel in an electrochemical process to generate electricity. Inadequate hydrogen concentration in the reactant fuel results in unsatisfactory fuel cell performance.

Hydrogen concentration sensors for fuel cells are known. Some such sensors rely on the Nernst Potential across two electrodes induced by a difference in hydrogen concentration at the respective electrodes. One shortcoming of that type of hydrogen sensor is that a reference electrode generates pure hydrogen as electrical current is applied to the reference electrode. Using the reference electrode to evolve pure hydrogen in this way tends to introduce potential shifts at the reference electrode, which interferes with accurate hydrogen concentration measurement.

SUMMARY

An illustrative example hydrogen concentration sensor includes a hydrogen chamber configured to isolate hydrogen within the hydrogen chamber from gas outside the hydrogen chamber. A hydrogen evolving electrode is configured to generate pure hydrogen within the hydrogen chamber. A reference electrode is situated to be exposed to pure hydrogen within the hydrogen chamber. A detection electrode associated with the reference electrode is situated to be exposed to gas outside the hydrogen chamber. The detection electrode is configured to provide an indication of a concentration of hydrogen in the gas outside the hydrogen chamber.

In an example embodiment having one or more features of the hydrogen concentration sensor of the previous paragraph, the hydrogen evolving electrode introduces a positive pressure within the hydrogen chamber.

In an example embodiment having one or more features of the hydrogen concentration sensor of any of the previous paragraphs, the hydrogen chamber includes a vent. The positive pressure within the hydrogen chamber prevents the gas outside the hydrogen chamber from entering the hydrogen chamber through the vent.

In an example embodiment having one or more features of the hydrogen concentration sensor of any of the previous paragraphs, the hydrogen evolving electrode is part of a first electrochemical cell and the reference electrode and the detection electrode are part of a second electrochemical cell.

In an example embodiment having one or more features of the hydrogen concentration sensor of any of the previous paragraphs, the first electrochemical cell comprises a first matrix containing an electrolyte. The first electrochemical cell comprises a hydrogen oxidizing electrode. The first matrix is at least partially situated between the hydrogen oxidizing electrode and the hydrogen evolving electrode. A voltage is applied across the hydrogen evolving electrode and the hydrogen oxidizing electrode.

In an example embodiment having one or more features of the hydrogen concentration sensor of any of the previous paragraphs, the electrolyte in the first matrix comprises phosphoric acid.

In an example embodiment having one or more features of the hydrogen concentration sensor of any of the previous paragraphs, the second electrochemical cell includes a second matrix at least partially situated between the reference electrode and the detection electrode. A voltage across the reference electrode and the detection electrode provides the indication of the concentration of hydrogen in the gas outside the hydrogen chamber.

In an example embodiment having one or more features of the hydrogen concentration sensor of any of the previous paragraphs, the second matrix contains phosphoric acid.

In an example embodiment having one or more features of the hydrogen concentration sensor of any of the previous paragraphs, positive pressure within the hydrogen chamber prevents the gas outside the hydrogen chamber from entering the hydrogen chamber.

In an example embodiment having one or more features of the hydrogen concentration sensor of any of the previous paragraphs, no current passes at the reference electrode.

An illustrative example method of determining a concentration of hydrogen in a gas includes evolving pure hydrogen from the gas using a hydrogen evolving electrode, at least temporarily containing the evolved pure hydrogen in a hydrogen chamber, exposing a reference electrode to the pure hydrogen in the hydrogen chamber, exposing a detection electrode to the gas, and determining a voltage across the reference electrode and the detection electrode as an indication of the concentration of hydrogen in the gas.

In an example embodiment having one or more features of the method of the previous paragraphs, the hydrogen evolving electrode is associated with a hydrogen oxidizing electrode and the method comprises exposing a hydrogen oxidizing electrode to the gas and applying a voltage across the hydrogen oxidizing electrode and the hydrogen evolving electrode.

In an example embodiment having one or more features of the method of any of the previous paragraphs, the method includes introducing a positive pressure within the hydrogen chamber and isolating the pure hydrogen in the hydrogen chamber from the gas using the positive pressure.

In an example embodiment having one or more features of the method of any of the previous paragraphs, the hydrogen evolving electrode introduces the positive pressure within the hydrogen chamber.

In an example embodiment having one or more features of the method of any of the previous paragraphs, the hydrogen chamber includes a vent. The positive pressure within the hydrogen chamber prevents the gas outside the hydrogen chamber from entering the hydrogen chamber through the vent.

In an example embodiment having one or more features of the method of any of the previous paragraphs, the hydrogen evolving electrode is part of a first electrochemical cell. The first electrochemical cell comprises a first matrix containing an electrolyte. The first electrochemical cell comprises a hydrogen oxidizing electrode. The first matrix is at least partially situated between the hydrogen oxidizing electrode and the hydrogen evolving electrode. The method comprises applying a voltage across the hydrogen evolving electrode and the hydrogen oxidizing electrode.

In an example embodiment having one or more features of the method of any of the previous paragraphs, the reference electrode and the detection electrode are part of a second electrochemical cell. The second electrochemical cell includes a second matrix at least partially situated between the reference electrode and the detection electrode. The second matrix contains phosphoric acid.

In an example embodiment having one or more features of the method of any of the previous paragraphs, the gas is in a fuel cell power plant reformer and the method comprises determining an operating condition of the reformer based on the determined concentration of hydrogen in the gas and adjusting operation of the reformer based on the operating condition.

In an example embodiment having one or more features of the method of any of the previous paragraphs, determining the operating condition and adjusting the operation are performed independent of determining a temperature in the reformer.

Various features and advantages of at least one disclosed example embodiment will become apparent to those skilled in the art from the following detailed description. The drawings that accompany the detailed description can be briefly described as follows.

BRIEF DESCRIPTION OF THE DRAWINGS

FIG. 1 schematically illustrates an example hydrogen concentration sensor designed according to an embodiment of this invention.

FIG. 2 schematically illustrates another example embodiment of a hydrogen concentration sensor.

FIG. 3 schematically illustrates selected portions of a fuel cell power plant including a hydrogen concentration sensor designed according an embodiment of this invention.

DETAILED DESCRIPTION

Hydrogen concentration sensors designed according to an embodiment of this invention are useful for a variety of purposes. Determining hydrogen concentration for a fuel cell power plant is one example implementation that is discussed below. One feature of embodiments of this invention is that a hydrogen evolving electrode that is distinct from a reference electrode evolves pure hydrogen into a hydrogen chamber where the reference electrode is exposed to the pure hydrogen. This avoids applying any current to the reference electrode and facilitates maintaining a consistent reference potential at the reference electrode, which results in improved sensor performance compared to previous sensors.

FIG. 1 shows an example hydrogen concentration sensor 20. A hydrogen evolving electrode 22 is part of a first electrochemical cell 24 that also includes a hydrogen oxidizing electrode 26 and a matrix 28. In this example, the matrix 28 contains a liquid electrolyte, such as phosphoric acid. The hydrogen evolving electrode 22 introduces pure hydrogen into a hydrogen chamber 30 when a voltage is applied across the hydrogen oxidizing electrode 26 and the hydrogen evolving electrode 22. In the illustrated example the applied voltage is approximately 0.3 volts.

A reference electrode 32 is situated to be exposed to the pure hydrogen in the hydrogen chamber 30. The reference electrode 32 is part of a second electrochemical cell 34 that also includes a detection electrode 36 and a matrix 38. The matrix 38 in this example also contains a liquid electrolyte, such as phosphoric acid.

The detection electrode 36 is exposed to gas outside the hydrogen chamber 30 and provides an indication of a concentration of hydrogen in that gas. The illustrated example embodiment utilizes the known Nernst Potential phenomenon as a basis for determining the hydrogen concentration outside of the hydrogen chamber 30. A potential difference (i.e., a voltage) across the detection electrode 36 and the reference electrode 32 provides an indication of the concentration of hydrogen in the gas outside the hydrogen chamber 30.

In the illustrated example, the hydrogen oxidizing electrode 26 and the detection electrode 36 are exposed to the same gas. At least some hydrogen from that gas is introduced into the hydrogen chamber 30 by the hydrogen evolving electrode 22. The first electrochemical cell 34 reduces protons based on the hydrogen oxidizing electrode 26 being exposed to the gas outside the hydrogen chamber 30. The hydrogen oxidizing electrode 26 has a size and position relative to the detection electrode 36 that does not alter the hydrogen concentration in the gas near the detection electrode 36 to avoid skewing the hydrogen concentration measured by the sensor 20.

In the illustrated example, the pure hydrogen in the hydrogen chamber 30 is kept from mixing with gas outside the hydrogen chamber 30 by positive pressure within the hydrogen chamber 30. The hydrogen evolving electrode 32 introduces a positive pressure within the hydrogen chamber 30. The size of the hydrogen evolving electrode 32, the amount of pure hydrogen introduced into the hydrogen chamber 30 over time, or both is selectable to provide a desired level of positive pressure within the hydrogen chamber 30.

The example hydrogen chamber 30 includes a vent 40 that allows pure hydrogen to exit the hydrogen chamber 30. The positive pressure within the hydrogen chamber 30 prevents any gas outside the hydrogen chamber 30 from entering the chamber.

One feature of the illustrated example is that the reference electrode 32 is distinct from the hydrogen evolving electrode 22. Using the hydrogen evolving electrode 22 to provide the pure hydrogen that keeps the reference electrode 32 at a desired reference potential avoids any need to apply current to the reference electrode. This feature eliminates any shifts in the reference potential that would otherwise occur if the reference electrode 32 were used to evolve pure hydrogen. Having the reference electrode 32 exposed to only pure hydrogen in the hydrogen chamber 30 also ensures a desired potential resulting from the exposure of the reference electrode 32 to the pure hydrogen.

Another sensor configuration is shown in FIG. 2. In this example, the hydrogen evolving electrode 26 and the detection electrode 36 are situated on opposite sides of the sensor 20. This embodiment operates in the same manner as the one shown in FIG. 1.

Hydrogen concentration sensors embodying this invention can be used in a variety of contexts and for various purposes. FIG. 3 shows one example implementation in which a sensor 20 is included in a fuel cell power plant 50. A reformer 52 receives a hydrocarbon 54, which may be methane or natural gas for example. The reformer 52 produces a hydrogen fuel at 56 that is supplied to a fuel cell stack assembly 58. The hydrogen fuel is one of the reactants used by the fuel cell stack assembly 58 and oxygen, which may be supplied as air 60, is the other reactant. A hydrogen concentration sensor 20 within the reformer 52 provides information regarding the operation of the reformer 52. A reformer control 62, such as a microprocessor or other computing device, uses the information from the sensor 20 for dynamically adjusting or tuning the operation of the reformer 52. The control 62 does not require any temperature information in this example embodiment, which can provide cost savings compared to systems that require temperature sensors and processing temperature information.

Hydrogen concentration sensors designed according to an embodiment of this invention are more stable and therefore more reliable than previous sensors that utilize a reference electrode that depends on pure hydrogen to establish the reference potential. Additionally, sensors designed according to an embodiment of this invention can be included in a wider variety of situations where hydrogen level detection is desirable.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A fuel cell power plant, comprising:
a fuel cell stack;
a reformer configured to produce hydrogen fuel for the fuel cell stack;
a hydrogen concentration sensor that detects hydrogen concentration in a hydrogen fuel supplied in a supply line to the fuel cell stack; and
a controller that is configured to dynamically adjust operation of the reformer such that the reformer produces hydrogen fuel that is supplied in the supply line to the fuel cell stack based, at least in part, on an indication from the hydrogen concentration sensor,
the hydrogen concentration sensor comprising:
a hydrogen chamber configured to isolate hydrogen within the hydrogen chamber from gas outside the hydrogen chamber;
a hydrogen evolving electrode configured to generate pure hydrogen within the hydrogen chamber;
a reference electrode situated to be exposed to the pure hydrogen within the hydrogen chamber; and
a detection electrode associated with the reference electrode, the detection electrode being situated to be exposed to the gas outside the hydrogen chamber, the detection electrode being configured to provide an indication of a concentration of hydrogen in the gas outside the hydrogen chamber,
wherein
the hydrogen evolving electrode is part of a first electrochemical cell,
the reference electrode and the detection electrode are part of a second electrochemical cell,
the first electrochemical cell includes a first matrix containing a liquid electrolyte,
the second electrochemical cell includes a second matrix containing a liquid electrolyte, and
the first and second electrochemical cells are disposed on a common side of the hydrogen chamber and are separated by a gap established by a wall that protrudes into the hydrogen chamber to establish a constriction between a first region of the hydrogen chamber associated with the hydrogen evolving electrode and a second region of the hydrogen chamber associated with the reference electrode.

2. The fuel cell power plant of claim 1, wherein the hydrogen evolving electrode introduces a positive pressure within the hydrogen chamber.

3. The fuel cell power plant of claim 2, wherein
the hydrogen chamber includes a vent; and
the positive pressure within the hydrogen chamber prevents the gas outside the hydrogen chamber from entering the hydrogen chamber through the vent.

4. The fuel cell power plant of claim 3, wherein the vent is established along the second region of the hydrogen chamber.

5. The fuel cell power plant of claim 1, wherein
the first electrochemical cell comprises a hydrogen oxidizing electrode;
the first matrix is at least partially situated between the hydrogen oxidizing electrode and the hydrogen evolving electrode; and
a voltage is applied across the hydrogen evolving electrode and the hydrogen oxidizing electrode.

6. The fuel cell power plant of claim 5, wherein the liquid electrolyte in the first matrix comprises phosphoric acid.

7. The fuel cell power plant of claim 5, wherein
the second matrix is at least partially situated between the reference electrode and the detection electrode; and
a voltage across the reference electrode and the detection electrode provides the indication of the concentration of hydrogen in the gas outside the hydrogen chamber.

8. The fuel cell power plant of claim 7, wherein positive pressure within the hydrogen chamber prevents the gas outside the hydrogen chamber from entering the hydrogen chamber.

9. The fuel cell power plant of claim 7, wherein no current passes at the reference electrode.

10. The fuel cell power plant of claim 1, wherein
the second matrix is at least partially situated between the reference electrode and the detection electrode; and
a voltage across the reference electrode and the detection electrode provides the indication of the concentration of hydrogen in the gas outside the hydrogen chamber.

11. The fuel cell power plant of claim 10, wherein the liquid electrolyte in the second matrix comprises phosphoric acid.

12. The fuel cell power plant of claim 1, wherein positive pressure within the hydrogen chamber prevents the gas outside the hydrogen chamber from entering the hydrogen chamber.

13. The fuel cell power plant of claim 1, wherein no current passes at the reference electrode.

* * * * *